United States Patent [19]

Allain et al.

[11] 4,375,003
[45] Feb. 22, 1983

[54] METHOD FOR THE HYDROGENATION OF NITRILES TO PRIMARY AMINES

[75] Inventors: Ronald J. Allain; Gerald D. Smith, both of Richmond, Tex.

[73] Assignee: Nalco Chemical Company, Oak Brook, Ill.

[21] Appl. No.: 3,138

[22] Filed: Jan. 15, 1979

Related U.S. Application Data

[63] Continuation of Ser. No. 924,327, Jul. 13, 1978, abandoned, which is a continuation of Ser. No. 841,501, Oct. 11, 1977, abandoned, which is a continuation of Ser. No. 743,731, Nov. 22, 1976, abandoned.

[51] Int. Cl.$^3$ .............................................. C07C 85/12
[52] U.S. Cl. ................................ 564/492; 252/477 Q; 564/491; 564/493
[58] Field of Search ............... 260/583 K; 252/477 Q; 564/490

[56] References Cited

U.S. PATENT DOCUMENTS 2,604,455 7/1952 Reynolds et al. .......... 252/477 Q X
3,943,171 3/1976 Hoffmann et al. .......... 252/477 Q X
3,972,940 8/1976 Morgan, Jr. .................... 260/583 K
4,014,820 3/1977 Svarz et al. ................. 252/477 Q X

FOREIGN PATENT DOCUMENTS 43-27744 11/1968 Japan .............................. 252/477 Q
1164354 9/1969 United Kingdom ................ 260/583

OTHER PUBLICATIONS

Khim Prom. No. 7,399-401 (1958) By P. A. Moshkin et al.

Primary Examiner—Jacqueline V. Howard
Attorney, Agent, or Firm—John G. Premo; Robert A. Miller

[57] ABSTRACT

An improved process for preparing primary amines from an aliphatic nitrile and hydrogen utilizing a Raney cobalt catalyst which contains from about 2 to 35 weight percent of aluminum on a 100 weight percent total weight basis. Preferably, this catalyst is prepared under low temperature conditions from a cobalt-aluminum alloy. The process can be practiced continuously for extended periods of time at high reaction rates and high conversion yields even when employing concentrated nitrile starting feeds.

17 Claims, No Drawings

METHOD FOR THE HYDROGENATION OF NITRILES TO PRIMARY AMINES

This is a continuation of application Ser. No. 924,327 filed on July 13, 1978, now abandoned, which in turn is a continuation of Ser. No. 841,501 filed 10-11-77 now abandoned, which in turn is a continuation of Ser. No. 743,731 filed: 11-22-76 now abandoned.

BACKGROUND OF THE INVENTION

In the art of catalytically reducing lower aliphatic nitriles with hydrogen to prepare the corresponding primary amine, various catalysts have been proposed. Among the catalysts which have been mentioned include skeletal cobalt catalysts such as that found in Khim Prom. No. 7, 399–401 (1958) and U.S. Pat. No. 3,972,940 which suggests the use of a Raney cobalt and Raney nickel catalysts for the hydrogenation of nitriles to their corresponding amine derivative. There has, however, been a serious problem with the selectivity and reactivity of prior art Raney cobalt catalyst, and under some circumstances, it has been necessary to conduct these reactions in the presence of a basic substance (ammonia) which is both time consuming and costly. Other problems have been selectivity toward the preparation of primary amines and low yields. While Raney type catalysts have been known in the prior art, it is now believed that the conditions for the preparation of this material have a profound effect on catalytic activity. A Raney cobalt catalyst which is highly selective, produces primary amines in high yield, and which will not need external feeds of ammonia or other bases to increase catalytic activity would therefore be highly desirable.

BRIEF SUMMARY OF THE INVENTION

The present invention is directed to an improved catalytic process for preparing aliphatic amines by the hydrogenation of an aliphatic nitrile. Typically, such a starting composition comprises the nitrile, and possibly an unreactive organic solvent, in the presence of a hydrogen feed source. The process is conducted under liquid phase conditions using temperatures of about 30°–300° C. with temperatures of from about 50°–170° C. being preferred. The pressure employed in a process of this type generally ranges from about 50–1,000 psi and most preferably from about 100–500 psi.

The process involves contacting each composition with particular type of Raney cobalt catalyst. This catalyst comprises from about 2 to 35 weight percent aluminum with the balance up to 100 weight percent being cobalt. More preferably, such catalyst comprises, on a 100 weight percent total weight basis, from about 2 to 30 weight percent aluminum with the balance up to 100 weight percent being cobalt. The catalyst has an average particle size in the range from about 0.002 to 0.5 inches. The catalyst is prepared by the particular process enumerated in this disclosure.

Because of the characteristically high initial catalytic activity and the characteristically long life associated with a catalyst when used in the process of this invention wherein an aliphatic nitrile is hydrogenated to its corresponding primary amine, the present invention provides an improved catalytic hydrogenation process which can be operated continuously and with extended periods of time with the same catalyst to produce desired, economically significant, high conversion yields of aliphatic primary amines at economically significant high rates of conversion. The invention is particularly useful, and the foregoing advantages are well demonstrated when using starting compositions containing a nitrile which often forms secondary amine by-products on hydrogenation.

In addition, the process of this invention offers operating efficiencies and economics, particularly in fixed bed catalytic processes. The process also allows continuous operations which are believed greater than heretofore known in the art.

The present invention provides an improved technique for activating a Raney cobalt catalyst for use in a process for hydrogenating aliphatic nitriles to their corresponding aliphatic primary amines under liquid phase conditions.

Further, the present invention aims to provide a Raney cobalt catalyst which permits one to hydrogenate aliphatic nitriles to their corresponding primary amines in a process substantially free of by-product formation achieving a higher initial activity together with a longer catalyst life than has heretofore been possible.

It is, therefore, an object of this invention to provide to the art an improved Raney cobalt catalyst for the hydrogenation of nitriles to their corresponding primary amine.

A further object of this invention is to provide to the art a highly specific and improved process for the hydrogenation of nitriles to primary amines using a Raney cobalt catalyst having improved properties.

Other objects will appear hereinafter.

Other and further aims, objects, purposes, advantages, utilities and features will be apparent to those skilled in the art from a reading of the present specification and drawings.

DETAILED DESCRIPTION

The catalyst used in the practice of the present invention is a Raney cobalt foraminous catalyst which has been specially activated. The starting material for this catalyst is a preformed binary Al/Co alloy which contains a weight percent ratio of Al/Co in the range from about 70:30 to 30:70 (preferably about 45:55 to 55:45, and most preferably about 50:50). The alloy particles have average particle diameters in the range of from about 0.002 to 0.5 inch.

This catalyst is, in general, preparable by contacting a group of cobalt-aluminum alloy particles with a liquid aqueous medium containing dissolved therein alkali metal hydroxide. The contacting is done while maintaining a reaction rate between said particles and said hydroxide in said medium such that less than about 0.02 (preferably less than about 0.01) moles of hydrogen per mole of said aluminum initially present in said alloy on a 100 weight percent total initial alloy basis is evolved per minute. The contacting is conducted while keeping the bulk temperature in said medium in the region of said group in the range from about 0°–50° C., and preferably 0°–35° C., and this contacting is continued until at least about 25 weight percent of said aluminum initially present in said alloy on a 100 weight percent total initial alloy basis is removed.

Thus, in one mode, activation of this starting alloy is accomplished by prolonged time-wise addition (contacting) of an aqueous solution of alkali metal hydroxide (e.g., aqueous caustic) to a group of cobalt-aluminum alloy particles. Such alkali metal hydroxide solutions so added can contain from about 1 to 40 weight percent dissolved hydroxide. Solutions of alkali metal hydroxide having higher caustic contents (up to saturated solutions) may be employed as starting leaching compositions for use in the preparation (actuation) of the catalyst used in the present invention. Alkali metal hydroxide may also be added as solid pellets or flakes, although handling of alkali metal hydroxide as a solution is generally preferred on a commercial scale for reasons of safety and economy. During such addition, the alkali metal hydroxide (leaching compositions) reacts with and dissolves the aluminum in the starting alloy in amounts such that the amount of aluminum remaining in the so-leached solid catalyst product ranges from about 2 to 35 weight percent (based on total leached product weight), and preferably from about 9 to 30 weight percent, but at least about 25 weight percent of the aluminum, and preferably at least about 35 weight percent, thereof, initially present in said alloy on a 100 weight percent total initial alloy basis is removed.

In preparing the catalyst, the caustic solution and the resulting aqueous medium which contacts the cobalt-aluminum metal alloy have temperatures in the range from about 0°–50° C. The group of starting alloy particles has a particle size diameter in the range from about 0.002 to 0.5 inch, as indicated, and the cobalt-aluminum alloy has a starting cobalt to aluminum weight ratio of from about 30:70 to 70:30.

In this mode, the total time of contacting caustic solution with such particles is typically accomplished over a total time interval of from about 2 to 30 hours, although, longer times may be employed even up to 200 hours with the fresh or starting caustic solution preferably being added (contacted) gradually to such particles over this time interval. The starting alloy particles may be initially immersed in water before being contacted with caustic solution. The resulting aqueous medium to which the starting hydroxide solution is added can typically contain from about 0.5 to 40 weight percent (total medium basis) of dissolved alkali metal hydroxide; the starting alkali metal hydroxide solution can contain from about 1 to 50 weight percent, more or less, of dissolved alkali metal hydroxide. In this mode, the contact rate between a starting caustic (alkali metal hydroxide) solution and a group of cobalt-aluminum alloy particles ranges during such contacting from about 0.017 to 7.0 moles of caustic (alkali metal hydroxide) per mole of aluminum initially present in the alloy particles per hour.

As indicated, the alkali metal hydroxide is added incrementally to the reaction zone. It will be appreciated that the term "incrementally" as used herein is inclusive of both contiuous alkali metal hydroxide addition as well as discontinuous addition. Continuous alkali metal hydroxide is preferred for reasons of production simplicity. For present purposes, the contact rate is equivalent to the addition rate, generally, The total quantity of alkali metal hydroxide so added to the particle-contacting, alkali metal hydroxide medium ranges from about 0.5 to 20 moles of alkali metal hydroxide per mole of aluminum initially present in the alloy particles. After the alkali metal hydroxide has been completely added to such medium, the contacting is preferably continued.

In this mode of catalyst activation by incremental caustic addition, one can, for example, conveniently employ a total quantity of aqueous alkali metal hydroxide such that the total molar quantity of hydroxide used totals from about 1 to 5 times the total molar amount of aluminum it is desired to leach away, as when a batch preparation procedure is being employed where the aqueous hydroxide is being added to a vessel containing a fixed quantity of starting alloy, and such aqueous hydroxide leaching composition is allowed to accumulate in this vessel during the leaching operation. Alternatively, for example, one can employ a batch preparation procedure. In a procedure of this type, the aqueous hydroxide used is continuously removed from the region of the alloy being leached after contact therewith, and fresh aqueous hydroxide is continuously or intermittently brought into contact with such alloy being leached. One can also employ a larger total excess quantity of starting leaching composition during the leaching operation.

During the contacting of starting alloy with such leaching, composition, an aluminate (in solution or dispersion) and hydrogen gas are produced. Conveniently, the hydrogen gas is vented more or less at the rate generated from the reaction zone, and most of the aluminate is removed in the water of the leaching composition. As indicated, hydrogen evolution can be conventionally metered and used to control aluminum removal rate, if desired, but in general, the contacting conditions used in the one mode herein above described involving incremental caustic addition can be used to produce a catalyst for use in this invention without direct measurement of hydrogen evolution especially after reaction variables are once chosen and established within the ranges above indicated.

In another mode, and in fact the preferred mode, of catalyst activation to produce a catalyst having an aluminum content and an activity as indicated above one can employ temperature control rather than contacting rate as a primary means of controlling production of the desired catalyst from the starting alloy particles with an alkali metal hydroxide. When so using temperature control, those skilled in the art will appreciate that the alkali metal hydroxide aqueous medium initially contains at least about 1.0 weight percent dissolved alkali metal hydroxide (and preferably at least about 10.0 weight percent dissolved alkali metal hydroxide). The medium is preliminarily cooled to a temperature which is not above 35° C. before being contacted with the group of alloy particles. Optionally, substantially all of said alkali metal hydroxide can be initially present in such medium, and such medium is initially bulk added to a reaction zone wherein the alloy particles are contained, and the bulk temperature is maintained below about 50° C. during said contacting until at least about 25 weight percent, and preferably at least about 35 weight percent, (total initial alloy weight basis) of the aluminum is removed.

In catalyst activation using either incremental addition of caustic or low temperature, contacting is best achieved by maintaining the particles of alloy in a substantially fixed reaction zone. The particles may be in a substantially fixed spatial position or if small enough, they may be suspended in the fixed reaction zone in the alkaline aqueous reaction medium by means of agitation, medium circulation, or the like. Thus the alkaline medium can be continuously agitated, or when the particles are maintained in a relatively fixed spatial position, the medium can be circulated through and around such. It is preferred to avoid masses of particles to minimize deleterious heat exposure thereof.

As the base for use in the catalyst activation procedure, one can employ any alkali metal hydroxide; however, for reasons of commercial availability, it is preferred to employ the sodium and potassium hydroxides industrially used and generally available commerically. It is preferred to conduct the activation operation under inert, nonoxidizing, atmosphere conditions, such as under a blanket of nitrogen gas, or a gas of the helium family.

The catalyst for use in this invention is generally prepared in a contact time interval with aqueous alkali metal hydroxide solutions which ranges from about 2 to 30 hours, and preferably from about 6 to 12 hours.

In catalyst activation by this invention, a group of alloy particles is confined to a reaction zone, and a solution of the base used for catalyst activation is added into the reaction zone. The resulting solution produced in contacting is allowed to accumulate in the zone. The starting group of alloy particles may be initially wet with water, or may be initially substantially free from water, as desired. In one preferred mode the particles are initially immersed in water before contact with caustic. Catalyst activation is preferably conducted under conditions which minimize the rate of heat release from the highly exothermic reaction between base and starting alloy. As indicated, one convenient procedure is to employ small, incremental charges of leaching solutions during the reaction. In some instances, as indicated, the amount of aluminum removed may be monitored by measuring hydrogen evolved during the reaction. In other instances, analysis of the aluminum in the base solution may be used as a measure of aluminum removal from the alloy.

It is important within the course of this invention, regardless of method chosen for catalyst activation, that the temperature of the aqueous medium be held below about 50° C., and preferably below about 35° C. A preferred temperature range is between 0°–35° C.

After the alloy has thus been activated with base (alkali metal hydroxide solution), it is then washed with water, preferably deionized or distilled, primarily to separate therefrom any remaining unreacted caustic. Conveniently, the resulting solid catalyst particles remaining are washed with water to a neutral pH (e.g., a pH below about 7.5 and preferably in the range of from about 7.0 to 7.5). The catalyst can then be removed from the reaction or activation zone, as is, or in the preferred method, can be wet screened to separate fines. The resulting catalyst product can be stored conveniently under water which prevents atmospheric oxidation thereof.

For use in this invention, the washed catalyst is contacted with the nitrile desired to be converted to its corresponding primary amine in the presence of a hydrogen gas feed. The hydrogenation reaction proceeds even when the amount of catalyst used in this invention is very slight. The greater the amount of catalyst used, the faster the reaction proceeds, other variables being constant. Consequently, the amount of catalyst employed per mole of starting nitrile initially employed can preferably range from about 0.01 to 100 g.

Primary amines may be made from the mixture of nitrile and hydrogen in accordance with the present invention using a suspension bed, or a fixed bed of catalyst, or combination thereof. Two or more reactors may be connected in series, and the reaction liquid containing the catalyst particles, as when a suspension bed system is employed, may be counter-currently moved to effect and enhance the reaction.

The hydrogenation process of this invention may be practiced at pressures of from 50–1,000 psi, and preferably from 125–500 psi, the latter being preferred; however, the process also may be practiced at desired superatmospheric pressures depending upon equipment considerations. When practicing the process of the present invention using a Raney cobalt catalyst prepared as described herein and utilizing a suspension bed system, it is preferred to employ the Raney cobalt catalyst in the form of particles having average particle diameters in the range from about 0.002 to 0.100 inch. Similarly, when the present invention is practiced using the Raney cobalt catalyst in the form of a fixed bed, it is convenient and preferred to use the Raney cobalt catalyst in the form of particles having average particle diameters in the range from about 0.02 to 0.5 inch.

In another preferred catalyst preparation procedure, using the preferred route above described, the alloy particles are confined to a reaction zone. The caustic solution is first contacted with the group of particles of the zone and the resulting aqueous medium is gradually removed from the zone.

In another, more preferred, catalyst preparation procedure, using the preferred route above described, the resulting aqueous medium is so removed at a volumetric rate which is about equal to the rate of addition of said caustic solution.

In such a preferred procedure, substantially 100 weight percent of this so removed resulting aqueous medium can be recycled back into contact with the group of particles being activated. During such a recycle, the so recycled aqueous medium is admixed with at least a portion of fresh caustic solution before or during recycle contact with such group of particles.

Alternatively, less than 100 weight percent of the so removed resulting aqueous medium can be recycled back into contact with the group of particles. The balance up to 100 weight percent thereof is removed from the reaction zone and can be discarded. Caustic is preferably gradually added at a rate approximately equal to the rate at which the caustic is consumed through reaction with the aluminum in the alloy. The process may preferably be practiced continuously at a rate which is approximately equal to the rate of consumption.

When practicing the present invention, it is preferred to prepare a catalyst with relatively large particles and to use a fixed bed catalyst in the reaction zone or zones employed. The amount of aluminum left in the catalyst after an activation, as described herein, can vary widely, but, in the case of an active catalyst used for fixed bed catalysts, it has been found that as much as about 9 to 30 weight percent aluminum (based on total catalyst weight) can be present in a catalyst without apparently affecting catalyst use and performance characteristics, such as conversion rate, throughput rate of reactants, catalyst life, etc.

In preparing a catalyst for use in this invention, it will be appreciated that there is a very sensitive relationship between the temperature of activation and the time of caustic contact with starting alloy. In general, the higher the temperature the longer should be the time for caustic addition to provide an active catalyst because under such conditions localized overheating of the catalyst particles is avoided or reduced to a minimum level. Localized overheating of alloy particles is believed to interfere with generation of a catalyst having the desired characteristics associated with a Raney cobalt catalyst prepared as described in the present invention and used in the hydrogenation reaction as described in the present invention. If one employs a rapid reaction between alloy particles and alkali metal hydroxide so that the hydrogen evolution rate is greater than that employed in the practice of this invention there is characteristically produced a lessening of catalyst activity. When the caustic concentration exceeds about 20 percent of the liquid aqueous media, careful temperature control must typically be exercised. Most typically, the more concentrated the caustic solution, the lower should be the reaction temperature and the shorter the contact time of caustic with alloy.

It should be pointed out again that the temperature which is used to activate our catalyst ranges on the order from 0°–50° C. and is preferably kept at or lower than 50° C. A preferred range is between 0°–35° C.

The equipment utilized in the preparation of the Raney cobalt catalyst of our invention and methods for activation are similar to those pointed our for the activation of a Raney copper catalyst as prepared in U.S. Pat. No. 3,920,740 which is hereinafter incorporated by reference. It should be stated, however, that a Raney copper catalyst is not active for the purposes of this invention.

As used herein, the term "gradual" includes not only variations in process conditions but also incremental or intermittent addition of alkali to alloy particles, or removal of a resulting aqueous medium from the zone of a given activation reaction. As can be determined from the proceeding teachings, a reduction of the reaction rate of aluminum with caustic in generating a catalyst for use in this invention is desired in order to produce an active material. Such a reduction may be achieved, generally, by limiting the amount of caustic present so that the caustic is replaced in solution at a rate equal to the rate at which it is being consumed. In this way a deviation between the alloy particle temperature and the caustic temperature will be minimized, resulting in an active catalyst, as desired.

In a catalyst prepared as described herein for use in the process of this invention, the aluminum content is somewhat variable. In general, it is not necessary to remove substantially all of the aluminum present in the starting alloy. In general, a catalyst prepared for use in the present invention has at least two weight percent of aluminum contained therein. While the exact form of this aluminum from a chemical viewpoint is not known, it is possible that this aluminum is not in a pure metallic form but rather in the form of some compound or alloy with cobalt or other element.

It is a special feature of the present invention that relatively high quantities of aluminum can be present without interfering with the desired relative activity desired and needed in a catalyst used in the process of this invention as herein taught. In general, one can produce a catalyst having an aluminum content as high as 35 percent and still have relatively high catalyst activity.

In general, when preparing a catalyst by the procedure as described herein, it appears to be relatively easier to remove more aluminum from small sized starting alloy particles than it is to remove aluminum from larger sized alloy particles and still achieve relative activities as desired. In one preferred mode of preparing a catalyst for use in the process of this invention, one starts with alloy particles which have sizes in the range of from about 0.002 to 0.5 inches and the amount of aluminum removed from the particles through contact with aqueous alkali metal hydroxide is preferably between 35 percent and 90 percent of the aluminum initially present in the alloy particle, as conveniently determined through total hydrogen evolution during contacting or by the amount of soluble aluminum present in the aqueous alkali metal hydroxide medium after completing the contacting with the cobalt-aluminum alloy particles. Hence a preferred catalyst for use in the process of this invention has an aluminum content of from about 9 to 30 weight percent (total catalyst weight basis), and a particle size in the range of from about 0.002 to 0.5 inches. As those skilled in the art will appreciate a catalyst within the size range just given is particularly well adapted for use in the process of this invention when one is employing a fixed bed catalyst system.

In the activation of the catalyst of this invention, it is oftentimes advantageous to include zero up to about 25 weight percent based on the total solution, or the solubility limit thereof in water, whichever one is lower, of at least one aliphatic polyhydric alcohol containing at least two carbon atoms. A preferred aliphatic polyhydric alcohol compound for use in this invention contains at least three carbon atoms per molecule and at least three hydroxyl groups per molecule which are attached to at least three different carbon atoms. Such an alcohol typically contains less than nine carbon atoms per molecule which one preferred class of such aliphatic polyhydric alcohols is represented by the formula:

$$H-(CHOH)_n-H$$

where n is the integer of from 4 through 8 inclusive. More preferred compounds of the above formula are those where n is 5 to 6 and a most preferred class of compounds of the above formula are those where n is 6.

Preferred such alcohols have a solubility in water of at least about 5 weight percent. Generally, such alcohols have a molecular weight less than about 1,000, and preferably less than about 500, and when repeating or condensed molecules are combined into a single molecule, no more than a dimer or trimer is used.

While some alkali metal hydroxide during the contacting characteristically reacts with the aluminum of the alloy particles, the manner in which an aliphatic polyhydric alcohol functions in the practice of the present invention is presently unknown. One theory (and there is no intent herein to be bound by theory) is that an aliphatic polyhydric alcohol functions as a sequestering or stabilizing agent which prevents the precipitation of solid particles of alumina (or derivatives) on the surface or in the pores of the catalyst, a theory which may be supported by U.S. Pat. No. 2,345,134 where polyhydroxylated compounds apparently act as stabilizing agents for sodium aluminate. Particles previously contacted with an alkali metal hydroxide solution may advantageously be post-contacted with an aqueous solution of aliphatic hydroxylated hydrocarbon compound using concentrations as taught herein. These compositions are enumerated, and their method of use further exemplified in U.S. Pat. No. 3,929,673 hereinafter incorporated by reference.

Useful compounds within the course of this invention include; sorbitol, mannitol, pentaerythritol, glycerol, and ethylene glycol.

Nitriles useful for conversion to their corresponding primary amines within the course of this invention include those that are normally liquid at atmospheric temperatures and pressure and those which may be conveniently dissolved or dispersed in an inert organic solvent. Examples of nitriles of this type include aliphatic nitriles containing from 3–40 carbon atoms such as butyronitrile, propionitrile, and dodecyl nitrile among others. In addition, compounds having two or more nitrile groups may be hydrogenated in the course of this invention to their corresponding primary diamines. An illustrative example of a compound within this class is adiponitrile which upon hydrogenation will yield hexamethylene diamine. Other useful nitrile materials include those containing other molecules within the hydrocarbon chain such as oxygen. Examples of nitriles which are included in this class but which do not exclude others include; 3-methoxy propionitrile, 1,3-bis(2-cyanoethoxy)-2-propanol, tri-($\beta$-cyanoethyl)-nitro methane, 3-(N,N-dimethylamino)-propionitrile, 3-(N,N-diethylamino)-propionitrile, 3-(dodecylamino) propionitrile, and bis-(2-cyanoethyl) ether. It is understood that for the purpose of this invention all of the above classes of nitriles will be termed aliphatic nitriles.

In selecting a nitrile for use in this invention, the material should be liquid under normal conditions or should be soluble or readily dispersible in an inert organic solvent. Examples of solvents useful in the course of this invention include the aliphatic alcohols such as methanol, ethanol, and propanol, as well as the n-alkanes including pentane, hexane, heptane, octane, and higher molecular weight materials. Other materials may also be used so long as they remain inert under the reaction conditions and do not react with the primary amine being prepared.

While a base such as ammonia or alkali metal hydroxide may be employed during the course of the reaction to prevent the formation of secondary amine, the use of a base may cause the breakdown of the starting nitrile. A particular advantage of the catalyst of the instant invention is that no base need be employed to secure high yields and excellent selectivity to the primary amine product.

EMBODIMENTS

The present invention is further illustrated by reference to the following Examples. Those skilled in the art will appreciate that other and further embodiments are obvious and within the spirit and scope of this invention from the teachings of these present Examples taken with the accompanying specification.

EXAMPLE I

To a 3 l. round bottom flask equipped with a stirrer, thermometer, and addition funnel was charged 200 g of a 50:50 weight percent powdered alloy of cobalt-aluminum. The alloy was covered with 300 ml of deionized water. With slow stirring, a 50% solution of sodium hydroxide was added at a rate to maintain the reaction temperature of from 20°–35° C. After adding approximately 800 g of 50% caustic, the mixture was stirred overnight, washed to an approximate pH of less than 8 and stored. Active catalysts prepared in this manner contained 12–25% aluminum.

EXAMPLE II

The process of Example I was followed with the addition of 12.0 g of sorbitol to the 300 ml of deionized water. The final catalyst would have the properties enumerated in Example I.

EXAMPLE III

The process of Example I was followed with the addition of 12.0 g of gluconic acid to the 300 ml of deionized water. The final catalyst would have the properties enumerated in Example I.

EXAMPLE IV

Hydrogenation of nitriles was effected in a batch process employing a 2 l. Parr Autoclave. Reaction conditions were varied over a wide range of temperature, pressure, reaction time, catalyst load and solvent conditions. In general, 300 g of nitrile was completely reduced to the primary amine by stirring at 80° C. at 600 psi hydrogen pressure with 8% of the cobalt catalyst of this invention for 2½ hours. At the end of this period of time, the catalyst was recovered by filtration and the product analyzed by gas chromatography.

EXAMPLE V

This example will illustrate the batch hydrogenation of 3-(N,N-dimethylamino)-propionitrile. Utilizing the equipment described in Example IV, a 10% catalyst load of the catalyst prepared in Example II was used. Utilizing 300 psi hydrogen pressure at a temperature of 50° C., 100% primary amine was obtained in 0.25 hours. Under a similar set of conditions, a commercially available Raney nickel catalyst yielded 98% primary amine and 2% secondary amine. A commercially available Raney cobalt catalyst gave 99% primary amine but only 47% conversion after 2.5 hours.

EXAMPLE VI

Using the equipment described in Example IV, 3-(N,N-diethylamino)-propionitrile was hydrogenated using an 8% catalyst load of the catalyst of Example II. Using a temperature of 65° C. and 500 psi hydrogen pressure, 100% reduction of the nitrile to the corresponding amine (N,N-diethyl-1-3 diaminopropane) was obtained in 1.75 hours. A commercially available Raney nickel catalyst gave 100% conversion over the same period of time with 94% primary amine and 6% secondary amine product distribution. A commercially available Raney cobalt catalyst yielded over 99% primary amine but gave only 50% coversion after 1.75 hours reaction time at identical conditions.

EXAMPLE VII

The hydrogenation of 3-(dodecylamino)-propionitrile was carried out using the apparatus of Example IV at a temperature of 60° C. and 700 psi hydrogen pressure. A 4% catalyst load of the material of Example II was utilized. The desired diamine was obtained in high yield although some loss of starting materials occurred through breakdown to fatty amine and acrylonitrile.

EXAMPLE VIII

The catalyst of the instant invention was evaluated along with several other commercially available catalysts in the hydrogenation of butyronitrile to butyl amine. This was done to test the selectivity of the catalyst of the instant invention with and without the presence of a base such as ammonia. While it was known that other catalysts would perform utilizing a base, this generally requires higher pressure and higher temperature for a given reaction rate, additional equipment necessary for adding the base and/or recycling it, and introduces the possibility of reactant breakdown by catalyzing the equilibrium of cyanoethylation products and reactants. Therefore, a catalyst exhibiting high selectivity in the absence of added base and reasonable activity was sought. Various catalysts were prepared or purchased for evaluation in this hydrogenation. Generally, a 2 g sample of each catalyst was washed three times with methanol and placed in a 2 l. autoclave using 500 g of methanol for transfer and addition. The autoclave was then charged with 81 g of butyronitrile, pressurized to 400 psi with hydrogen at 125° C. Samples were collected at time intervals and evaluated by vapor phase chromatography. (See Table I)

TABLE I

| Catalyst[1] | Metal Analysis | Relative Activity[2] | Relative Selectivity[3] |
|---|---|---|---|
| Ex. II | 23.1% Al | 87.6 | 90.3 |
| Ex. II | 21.0% Al | 76.8 | 89.1 |
| Ex. III | 14.1% Al | — | 93.3 |
| A | 15.5% Al | 55.2 | 84.1 |
| A | 15.4% Al | 54.1 | 85.2 |
| B | 15.5% Al | 53.2 | 83.1 |
| C | Cobalt | 49.5 | 89.5 |
| D | 1.6% Cr 9.0% Al | 47.1 | 82.7 |
| E | 6.2% Mo 7.7% Al | 46.3 | 81.8 |
| F | 6.5% Al | 26.7 | 88.9 |
| F | 4.9% Al | 14.3 | 85.9 |
| G | 20.0% Cobalt | 2.3 | — |
| H | Cobalt | 0.8 | 60.1 |

[1]The catalysts were prepared or purchased and used fresh. Amounts were varied to give an equal charge of reactive metal.
[2]Relative activity was determined by measuring conversion of butyronitrile to butyl amine after two hours at 400 psi total pressure hydrogen and ammonia, 120 ± 5° C., and 1% catalyst load.
[3]Relative selectivity was determined by measuring the butyl amine and dibutyl amine distribution of the reaction product of butyronitrile after two hours at 400 psi hydrogen pressure, 120 ± 5° C., and 1% catalyst load.
Catalyst A:
This material was a commercially available Raney nickel catalyst designated as Grace 28.
Catalyst B:
This material was a nickel catalyst prepared in the same manner as the cobalt catalyst of the instant invention. This was an experimental material.
Catalyst C:
This material was a commercially available cobalt catalyst from the Strem Company designated cobalt 27-045.
Catalyst D:
This material was a commercially available nickelchromium catalyst designated as Garace 24.
Catalyst E:
This material was a commercially available Raney nickel catalyst containing molybdenum designated as Grace 30.
Catalyst F:
This material was a commercially available Raney cobalt catalyst designated as Grace 27.
Catalyst G:
This material was a commercially available cobalt catalyst designated as Harshaw 0405.
Catalyst H:
This material was a commercially available cobalt chromium catalyst designated as Girdler G-66.

EXAMPLE IX

The catalyst of Example II was utilized in the hydrogenation of butyronitrile with a 1.0% catalyst load at 130°±5° C., and 400 psi hydrogen for 150 minutes. A 100% conversion of butyronitrile to amine was achieved with 89.1% of this material being butyl amine. The catalyst contained 21.0% aluminum. In a similar run using identical conditions with a catalyst prepared according to Example II containing 23.1% of aluminum, 100% conversion was achieved with 90.3% selectivity to the primary amine. When a sample of the same catalyst was used at the identical conditions with the addition of ammonia, only 87.6% conversion was achieved with 97.9% of the material being the desired primary amine.

EXAMPLE X

This example is illustrative of the reactor utilized for continuous hydrogenation of nitriles to amines utilizing our invention. A reactor was constructed for the continuous reduction of nitriles over metal catalysts consisting of a 72 inch type 304 S.S. tube, 1.5 inch O.D., equipped with a 30 inch ¼ inch O.D. 304 S.S. thermowell at top and bottom, pressure gauge, and suitable fittings to allow concurrent downward flow of hydrogen and nitrile feed. The column pressure was controlled by inlet and outlet back pressure regulators to allow product to gently release to atmospheric conditions. The reactor temperature was vaired by passing a stream of steam downward, a mixture of steam and water upward, or circulating heated oil from a constant temperature bath thru copper tubing coiled around the reactor tube. Hydrogen feed was controlled with a Brooks High Pressure Gas Flowmeter and nitrile feed by a variable rate pump.

Generally, a catalyst load of 350 g of the catalyst of this invention spaced with four volumes of alumina balls was employed, onto which was pumped nitrile at a rate of 120 ml per hour. The reactor temperature was maintained at 65° C. and a pressure of 525 psi hydrogen provided at 2.1 SCFH. The desired product was usually obtained in excellent yield, with minor secondary amine formation.

The apparatus described above was utilized using a catalyst prepared by the method of Example II. Spaced in the reactor was 350 g of the catalyst having a particle size of 10 mesh along with four volumes of alumina balls. While maintaining the reactor temperature at 65° C. and a pressure of 525 psi hydrogen provided at 2.1 SCFH, 3-methoxypropionitrile was pumped onto the catalyst bed at a rate of 120 ml per hour. The desired product, 3-methoxypropylamine was formed in greater than 98% yield with less than 0.2% secondary amine formed.

We claim:

1. In an improved process for catalytically hydrogenating aliphatic nitriles to aliphatic primary amines by contacting the aliphatic nitrile with hydrogen in the presence of a Raney cobalt catalyst, the improvement which comprises:
   A. Contacting an aqueous medium containing dissolved therein an alkali metal hydroxide with a fixed group of cobalt-aluminum alloy particles, the alkali metal hydroxide being added incrementally to the aqueous medium during the contacting over a time interval,
      (1) said aqueous medium containing from about 0 to 50 weight percent dissolved alkali,
      (2) said group having an average particle diameter in the range of from about 0.002 to 0.5 inch,
      (3) said cobalt-aluminum alloy having an initial cobalt to aluminum weight ratio of from about 30:70 to 70:30,
      (4) said contacting being accomplished over a total interval of 2-30 hours,
      (5) the addition rate of alkali metal hydroxide solution being so added to said medium during said contacting being from about 0.01 to 7 moles alkali metal hydroxide per mole of aluminum initially in said alloy particles per hour,
      (6) the total quantity of alkali metal hydroxide so added being in the range of from about 0.5 to 20 moles of alkali metal hydroxide per mole of aluminum initially present in said alloy,
  (7) the resulting aqueous medium produced during said contacting being maintained at a temperature at or below about 50° C.;
B. Washing the so treated group of particles to separate therefrom remaining unreacted alkali metal until the resulting wash water has a pH of less than about 7.5; and then,
C. Contacting the so washed group of particles with an aliphatic nitrile containing 3–40 carbon atoms and hydrogen gas at a pressure of from 50–1,000 psi at a temperature of from 50° to 170° C. whereby the aliphatic nitrile is hydrogenated to the corresponding aliphatic primary amine.

2. The process of claim 1 wherein said group of particles is confined to a reaction zone and said alkali metal hydroxide solution is added into said reaction zone and said resulting medium is allowed to accumulate in said zone.

3. The process of claim 1 wherein said group of particles is initially wet with water.

4. The process of claim 1 wherein said group of particles is initially immersed with water.

5. In a process of the type wherein an aliphatic nitrile is hydrogenated with hydrogen in the presence of a cobalt catalyst to an aliphatic primary amine, the improvement which comprises using as said catalyst a Raney cobalt catalyst which contains from about 2 to 35% by weight on a 100 weight percent total catalyst weight basis of aluminum, said catalyst having been prepared by contacting an aqueous medium containing dissolved therein alkali metal hydroxide with a group of cobalt-aluminum alloy particles, the aqueous dissolved alkali metal hydroxide being added incrementally to the medium during the contacting over a time interval;
A. Said aqueous alkali metal hydroxide solution containing from 0.5 to 50 weight percent dissolved alkali;
B. Said group having an average particle diameter in the range of from about 0.002 to 0.5 inch;
C. Said cobalt-aluminum alloy having an initial cobalt to aluminum weight ratio of from about 30:70 to 70:30;
D. Said contacting being accomplished over a total interval of 2–30 hours;
E. The addition rate of alkali metal hydroxide solution being so added to said medium during said contacting being from about 0.01 to 7 moles alkali metal hydroxide per mole of aluminum initially in said alloy particles per hour;
F. The total quantity of alkali metal hydroxide so added being in the range of from about 0.5 to 20 moles of alkali metal hydroxide per mole of aluminum initially present in said alloy; and
G. The resulting aqueous medium produced during said contacting being maintained at a temperature at or below about 50° C.

6. In an improved process for selectively, catalytically hydrogenating aliphatic nitriles to their corresponding primary amine the improvement which comprises contacting said aliphatic nitrile with hydrogen in the presence of a Raney cobalt catalyst, said catalyst having been prepared by contacting a prechosen group of cobalt-aluminum alloy particles confined to a reaction zone with a liquid aqueous medium containing dissolved therein alkali metal hydroxide while maintaining a reaction rate between said particles and of said hydroxide such that not more than about 0.02 moles of hydrogen per mole of said aluminum initially present in said alloy on a 100 weight percent total initial alloy basis is evolved per minute, said contacting being contacted while keeping a bulk temperature in said medium in the region of said group ranging from about 0° to 50° C., said contacting being continued until at least about 35 weight percent of said aluminum initially present in said alloy on a 100 weight percent total initial alloy basis is removed, said alloy particles initially having a ratio of cobalt to aluminum in the range from about 30:70 to 70:30, said alloy particles further initially having average particle diameters in the range of from about 0.002 to 0.5 inch the total molar quantity of alkali metal hydroxide charged to said medium during the total time of said contacting being at least about 0.5 times the number of moles of aluminum initially present in said alloy particles, the total weight of water initially present in said medium at the beginning of said contacting plus water added to said medium during contacting ranges from about 1.5 to 100 times the total weight quantity of dissolved alkali metal hydroxide contacted with such particles.

7. The process of claim 6 wherein during said contacting,
A. Said alkali metal hydroxide is added to said medium incrementally at a rate which ranges from about 0.01 and 7.0 moles of alkali metal hydroxide per mole of aluminum initially present in said particles per hour,
B. The total quantity of alkali metal hydroxide being added to said medium ranges from about 0.5 to 20 moles of alkali metal hydroxide per mole of aluminum initially present in said group, and
C. Said addition of alkali metal hydroxide to said medium is conducted in a total time interval which ranges from about 2 to 200 hours.

8. The process of claim 6 wherein said particles are initially immersed in water before said contacting.

9. The process of claim 6 wherein, after said alkali metal hydroxide has been so added to said medium, said contacting is continued, the total time of contacting being for a period of time of not more than about 200 hours.

10. The process of claim 6 wherein during said contacting said alloy particles have average particle diameter ranging from about 0.002 to 0.5 inches, said contacting is achieved by maintaining said particles in a substantially fixed spatial position, and said medium is continuously circulated past said particles while said particles are so maintained.

11. The process of claim 6 wherein during said contacting said alloy particles have average particle diameters ranging from about 0.002 to 0.1 inch, and said particles and said medium are agitated to an extent sufficient to suspend said particles in said medium during said contacting.

12. The process of claim 1 wherein from 0 to 25% by weight of an aliphatic polyhydric alcohol is added prior to contacting the cobalt-aluminum alloy particles with the alkali metal hydroxide.

13. The process of claim 1 wherein from 0 to 25% by weight of an aliphatic polyhydric alcohol is present in the aqueous medium.

14. The process of claim 5 wherein from 0 to 25% by weight of an aliphatic polyhydric alcohol is added prior to contacting the cobalt-aluminum alloy particles with the alkali metal hydroxide.

15. The process of claim 5 wherein from 0 to 25% by weight of an aliphatic polyhydric alcohol is present in the aqueous medium.

16. The process of claim 6 wherein from 0 to 25% by weight of an aliphatic polyhydric alcohol is added prior to contacting the cobalt-aluminum alloy particles with the alkali metal hydroxide.

17. The process of claim 6 wherein from 0 to 25% by weight of an aliphatic polyhydric alcohol is present in the aqueous medium.

* * * * *